June 16, 1953 B. ENGKVIST Plant Pat. 1,196
ROSE PLANT
Filed July 18, 1952
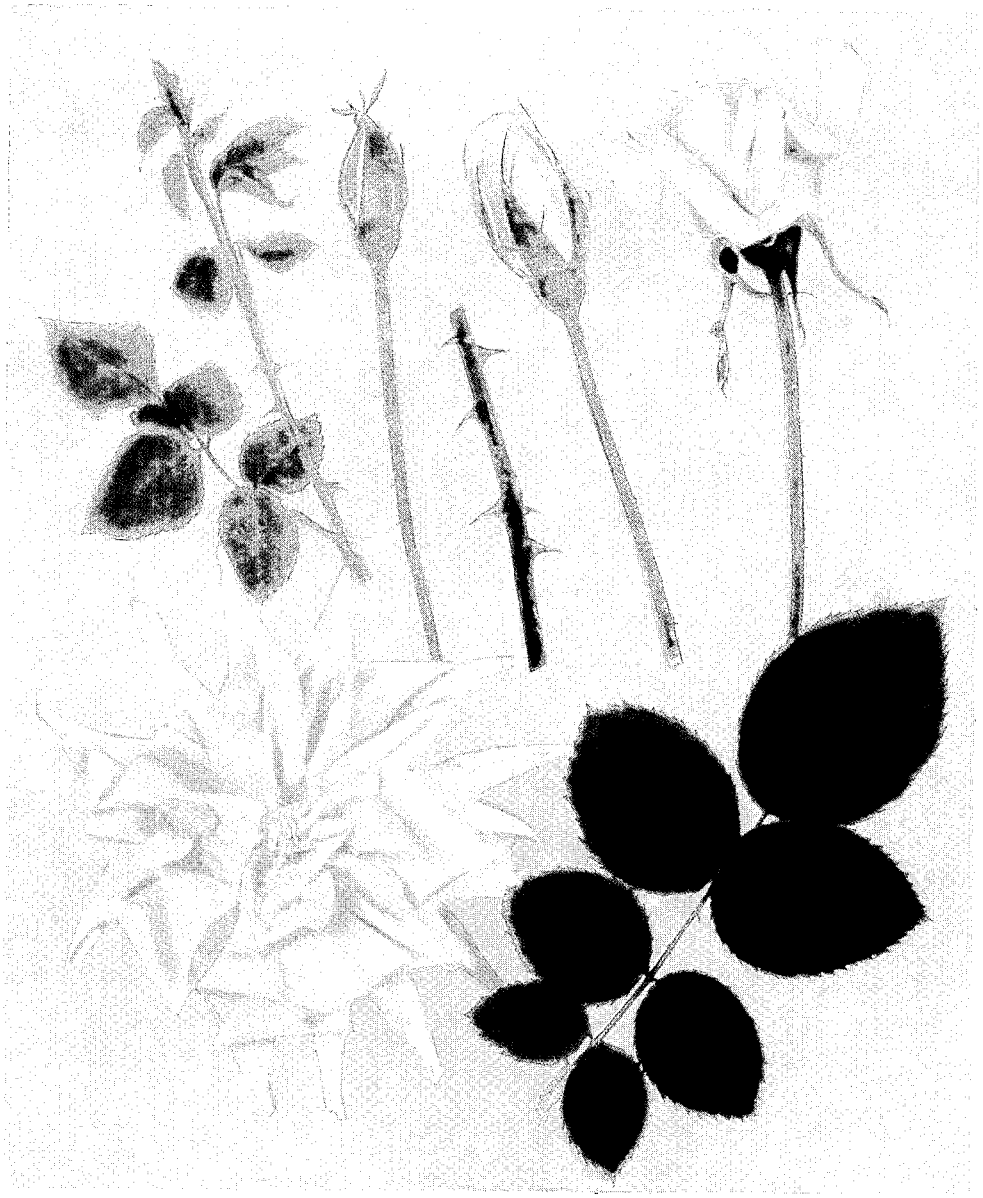
Inventor.
Bror Engkvist
By: Robert Cobb
Attorneys.

Patented June 16, 1953

Plant Pat. 1,196

UNITED STATES PATENT OFFICE 1,196

ROSE PLANT

Bror Engkvist, Halsingborg, Sweden, assignor, by mesne assignments, to Jackson & Perkins Company, Newark, N. Y., a corporation of New York Application July 18, 1952, Serial No. 299,782

1 Claim. (Cl. 47—61)

The present invention relates to a new and distinct variety of rose plant of the hybrid tea class, which was discovered by me amongst cultivated plantings of the variety "Orange Delight" (Plant Patent No. 874), being grown in greenhouses on my property in Sweden. My new variety occurred as a sport of the variety "Orange Delight," and I have found that it is importantly distinguished therefrom, as well as from all other varieties of its class, by the following outstanding characteristics which make it especially suitable as a greenhouse rose:

(1) The Peach Red general color tonality of its flowers, lightly overcast with Capucine Orange;

(2) An unusual and peculiar quilling characteristic of the petals of the flowers, which is very distinctive; and (3) The relatively quick growth and production of new flowers after each flower has been cut.

Asexual reproduction of this new variety by grafting in greenhouses at Newark, New York, U. S. A., shows that the foregoing characteristics and distinctions come true to form and are established and transmitted through succeeding propagations.

The accompanying drawing shows typical specimens of my new variety, with the flowers and foliage in different stages of development.

The following is a detailed description of my new variety, with color terminology in accordance with Ridgway's Color Standards and Nomenclature:

Parentage: Sport of "Orange Delight."
Classification:
*Botanic.*—Hybrid tea.
*Commercial.*—Hybrid tea.

*Flower*

Observations made in a greenhouse at Newark, New York, U. S. A., about mid-morning, near the middle of the month of December.)

Blooming habit: Recurrent—continuous, with a very short time between flowering periods.

Bud:
*Size.*—Medium.
*Form.*—Ovoid; is not affected by wet or hot weather.
*Color.*—When sepals first divide—Jasper Red, Plate 13. When petals begin to unfurl—Jasper Red, Plate 13, lightly overcast with Rose Doree, Plate 1, with the lower half of the petal having a slight overcast of Lemon Chrome, Plate 4. When half blown: inside of petals — Rose Doree, Plate 1, lightly overcast with Peach Red, Plate 1; reverse of petals—Peach Red, Plate 1, lightly overcast with Rose Doree, Plate 1.

*Sepals.*—Smooth edge; slightly branched; curl back when petals begin to unfurl. Color: inside—Absinthe Green, Plate 31; outside—Light Cress Green, Plate 31.
*Calyx.* — Shape — apple. Size — broad. Aspect—smooth. Odor when rubbed—none. Color—Lettuce Green, Plate 5.
*Peduncle.* — Length — medium. Aspect—prickly. Strength—erect; slender. Color—Lettuce Green, Plate 5.
*Opening.*—Opens up well; is not affected by adverse weather conditions.

Bloom:
*Size.*—Large. Average size when fully expanded—4½ inches to 5 inches.
*Borne.*—Singly and several together.
*Stems.*—Medium length; strong.
*Form.*—When first open—high center. Permanence—all petals curl quill fashion like a cactus dahlia.
*Petalage.*—Double (full but open center). Number of petals under normal conditions—35 to 45.
*Color.*—Center of flower—Peach Red, Plate 1. Outer petals—Strawberry Pink, Plate 1, lightly overcast with Capucine Orange, Plate 3. Base of petals (aiglet)—Lemon Chrome, Plate 4. Inside of petals—Peach Red, Plate 1, lightly overcast with Capucine Orange, Plate 3. Reverse of petals—Grenadine Pink, Plate 2, lightly overcast with Capucine Orange, Plate 3. General tonality from a distance—Peach Red, Plate 1, lightly overcast with Capucine Orange, Plate 3.
*Discoloration.*—General tonality at end of first day—Peach Red, Plate 1, lightly overcast with Capucine Orange, Plate 3. Second day—Grenadine Pink, Plate 2, lightly overcast with Capucine Orange, Plate 3. Third day—Strawberry Pink, Plate 1.

Petals:
*Texture.*—Thin; is not affected by wet or hot weather.
*Appearance.* — Inside — satiny; outside — shiny.
*Form.*—Oval.
*Arrangement.*—Informal (with "rags" in center). Petaloids in center—many; large.
*Persistence.*—Drop off cleanly.
*Fragrance.*—Slight. Nature—tea (average hybrid tea scent).
*Lasting quality.*—On the plant and as cut flower—long.

*Genital organs*

Stamens, anthers:
*Size*—Large.
*Arrangement.*—Mixed with petaloids.
*Color.*—Light Orange Yellow, Plate 3.

Stamens, filaments (threads):
*Length.*—Medium.
*Color.*—Apricot Yellow, Plate 4.
Pollen: Color—Maize Yellow, Plate 4.
Styles: Loosely separated; uneven length; medium length; thin.
Stigmas: Color—Maize Yellow, Plate 4.
Ovaries: All enclosed in calyx.

*Plant*

Form: Bush.
Growth: Vigorous; upright.
Foliage: 5 to 7 leaflets.
*Size.*—Medium.
*Quantity.*—Normal abundance.
*Color.*—New foliage: Upper side—Oil Green, Plate 5, lightly overcast with Pomegranate Purple, Plate 12, and serrations Pomegranate Purple, Plate 12; under side—Cosse Green, Plate 5, overcast with Pomegranate Purple, Plate 12, and serrations Pomegranate Purple, Plate 12. Old foliage: Upper side—Dark Cress Green, Plate 31; under side—Light Cress Green, Plate 31.
*Shape.*—Oval pointed.
*Texture.*—Upper side—smooth. Under side—rough. Ribs and veins—ordinary.
*Edge.*—Serrated (saw toothed).
*Serration.*—Double and single; small.
*Leaf stem.*—Color—Absinthe Green, Plate 31, lightly overcast with Oxblood Red, Plate 1. Under side—prickles.
*Stipules.*—Medium length; smooth.

Wood:
*New wood.*—*Color*—Pompeian Red, Plate 13. Bark—smooth.
*Old wood.*—Color—Cress Green, Plate 31. Bark—smooth.
Thorns:
*Thorns.*—Quantity: on main stalks from base—ordinary; on laterals from stalk—ordinary. Form—narrow base; medium length; hooked downward. Color when young—Eugenia Red, Plate 13. Position—irregular.
*Prickles.*—Quantity: on main stalks—few; on laterals—few. Color—Pale Lumiere Green, Plate 17.
*Short needles.*—On main stalks—none; on laterals—none.

I claim:

A new and distinct variety of rose plant of the hybrid tea class, substantially as herein shown and described, characterized as to novelty particularly by the Peach Red general color tonality, lightly overcast with Capucine Orange, of its flowers, by the distinctive quilling habit of the petals of its flowers, and by its relatively quick growth and rapid production of new flowers after each flower has been cut from the plant.

BROR ENGKVIST.

No references cited.